US006087491A

United States Patent [19]
Tang et al.

[11] Patent Number: 6,087,491
[45] Date of Patent: *Jul. 11, 2000

[54] EXTREMELY HIGH PURITY OLIGONUCLEOTIDES AND METHODS OF SYNTHESIZING THEM USING DIMER BLOCKS

[75] Inventors: Jin-Yan Tang; Nandkumar Bongle, both of Shrewsbury; Jose Gonzalez, Westborough; Warren E. Schwartz, Boxborough, all of Mass.

[73] Assignee: Hybridon, Inc., Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/827,561

[22] Filed: May 2, 1997

Related U.S. Application Data

[63] Continuation-in-part of application No. 08/339,918, Nov. 15, 1994, abandoned, which is a continuation of application No. 08/002,823, Jan. 8, 1993, abandoned.

[51] Int. Cl.$^7$ .................................................. C07H 21/00

[52] U.S. Cl. ....................................... 536/25.4; 536/25.34

[58] Field of Search ................................ 536/25.34, 25.4, 536/25.41, 25.42, 24.5, 26.6

[56] References Cited

U.S. PATENT DOCUMENTS

| | | | |
|---|---|---|---|
| 4,469,863 | 9/1984 | Ts'o et al. | 536/27 |
| 5,003,097 | 3/1991 | Beaucage et al. | 558/129 |
| 5,047,524 | 9/1991 | Andrus et al. | 536/27 |
| 5,149,798 | 9/1992 | Agrawal et al. | 536/27 |
| 5,252,723 | 10/1993 | Bhatt | 536/23.5 |
| 5,616,564 | 4/1997 | Rapaport et al. | 514/44 |

FOREIGN PATENT DOCUMENTS

| | | |
|---|---|---|
| 0136543 A2 | 4/1985 | European Pat. Off. . |
| 0219342 A3 | 9/1985 | European Pat. Off. . |
| 0241363 A1 | 10/1987 | European Pat. Off. . |
| 0386987 A1 | 9/1990 | European Pat. Off. . |
| 0552766 A2 | 1/1993 | European Pat. Off. . |
| WO 90/11322 | 10/1990 | WIPO . |
| WO 91/06556 | 5/1991 | WIPO . |
| WO 91/16902 | 11/1991 | WIPO . |
| WO 92/04358 | 3/1992 | WIPO . |
| WO 92/20697 | 11/1992 | WIPO . |
| WO 94/02499 | 2/1994 | WIPO . |
| WO 94/15946 | 7/1994 | WIPO . |
| WO 95/27718 | 10/1995 | WIPO . |
| WO 96/01268 | 1/1996 | WIPO . |

OTHER PUBLICATIONS

Agrawal et al., (1987) *Tetrahedron Lett.*, vol. 28, p. 3539.
Agrawal et al., (1988) *Proc. Natl. Acad. Sci.*, vol 85, p. 7079.
Agrawal et al., (1989) *Advanced Drug Delivery Reviews*, vol. 6, p. 251.
Agrawal et al., (1990) *Proc. Natl. Acad. Sci.*, vol. 87, p. 1401.
Agrawal et al., (1990) *Nucleic Acids Res.*, vol. 18, p. 5419.
Agrawal et al., (1990) *Tetrahedron Lett.*, vol. 31, No. 52, p. 7541–7544.
Agrawal et al., (1991) *Prospects for Antisense Nucleic Acid Therapy of Cancer and Aids*, p. 143.
Agrawal, *Tibtech*, vol. 14, p. 376.
Bannwarth, (1985) *Helv. Chim. Acta.*, vol. 68, p. 1907.
Barker et al., (1996) *Proc. Natl. Acad. Sci.*, vol. 93, p. 514.
Beaucage et al., (1981) *Tetrahedron Lett.*, vol. 22, p. 1859.
Bigelow et al., (1990) *J. Chromatography*, vol. 533, p. 131.
Connolly et al., (1984) *Biochemistry*, vol. 23, p. 3443.
Cosstick et al., (1985) *Biochemistry*, vol. 24, p. 3630.
Crea et al., (1978) *Prco. Natl. Aca. Sci.*, vol. 75, p. 5765.
Eckstein and Gish, (1989) *Trends Biochem.*, vol. 14, p. 97.
Field et al., (1995) *J. Exp. Opin. Invest. Drugs.*, vol. 4, p. 799.
Froehler et al., (1988) *Nuc. Acid. Res.*, vol. 16, No. 11, p. 4831–4839.
Helinski et al., (1991) *Tetrahedron Lett.*, vol. 32, p. 4981–4984.
Iyer et al., (1990) *J. Org. Chem.*, vol. 55, p. 4693–4699.
Jager et al., (1988) *Biochemistry*, vol. 27, p. 7237.
Kambhampati et al., (1993) *Antisnese Res. Dev.*, vol. 3, p. 405.
Katti et al., (1986) *Tetrahedron Lett.*, vol. 27, p. 5327.
Khorana et al., (1979) *Science*, vol. 203, p. 614.
Khorana et al., (1972) *J. Molec. Biol.*, vol. 72, p. 209.
Kumar et al., (1984) *J. Org. Chem.*, vol. 49, p. 4905.
Lebadev et al., (1990) *Tetrahedron Lett.*, vol. 31, p. 855.
Leiter et al., (1990) *Proc. Natl. Acad. Sci.*, vol. 87, p. 3430–3434.
Manson et al., *Lyphokine Res.*, vol. 9, p. 35.
Marugg et al., (1984) *Nucleic Acid Res.*, vol. 12, p. 9095.
Metelev et al., (1992) *Anal. Biochem.*, vol. 200, p. 342.
Metelev et al., (1992) *Ann. N.Y. Acad. Sci.*, vol. 660, p. 321–323.
Miura et al., (1987) *Chem. Pharm. Bull.*, vol. 35, p. 833.
Majumdar et al., (1989) *Biochemistry*, vol. 28, p. 1340.
Nesterova et al., (1995) *Nat. Med.*, vol. 1, p. 528.
Offensperger et al., (1993) *EMBO J.*, p. 1257.

(List continued on next page.)

*Primary Examiner*—Scott W. Houtteman
*Attorney, Agent, or Firm*—McDonnell Boehnen Hulbert & Berghoff

[57] ABSTRACT

The present invention comprises an improved method of synthesizing oligonucleotides. The method comprises employing dinucleotides (or "dimer blocks") as the basic synthetic unit building block. The method results in extremely high purity oligonucleotides in which the N–1 content is very low, generally less than 1–2% of the full length, N, oligonucleotide. We have found that synthesis using dinucleotide phosphorothioates results in oligonucleotides having very little phosphodiester content. Furthermore, we have found that the amount of dimer required in each coupling step can be less than about 6 and is preferably about 2 equivalents. Synthesis of oligonucleotides according to the dimer block approach described herein can also be conducted without the capping step that has heretofore been deemed necessary after each coupling.

1 Claim, No Drawings

OTHER PUBLICATIONS

Ohtsuka et al., (1982) *Nucleic Acids Res.*, vol. 10, p. 6553.
Reed et al., (1990) *Cancer Res.*, vol. 50, p. 6565.
Reese, (1978) *Tetrhedron Lett.*, vol. 34, p. 3143.
Roelen et al., (1988) *Nucleic Acids Res.*, vol. 16, p. 7633.
Roelen et al., (1992) *Tetrahedron Lett.*, vol. 33, p. 2357.
Stec et al., (1990) *J. Chromatography*, vol. 326, p. 263.
Uhlman et al., (1990) *Chem. Rev.*, vol. 90, p. 543.
Wolfgang et al., (1987) *Tetrahedron Lett.*, vol. 28, p. 3205–3208.

Wolter et al., (1986) *Nucleosides and Nucleotides*, vol. 5, p. 65.

Zamecnik et al., (1978) *Proc. Natl. Acad.*, vol. 75, p. 280.

Zamecnik et al., (1991) *Annual Review of AIDS Research*, p. 301.

Krotz et al., (1996) *Bioorganic & Medicinal Chemistry Letters*, vol. 7, No. 1, p. 73–78.

Krotz et al., Bioorg. Med. Chem. Lett. 7(1):73–78, Abstract, Jan. 1997.

EXTREMELY HIGH PURITY OLIGONUCLEOTIDES AND METHODS OF SYNTHESIZING THEM USING DIMER BLOCKS

This application is a continuation-in-part of U.S. application Ser. No. 08/339,918, filed on Nov. 15, 1994, now abandoned, which is a continuation of U.S. application Ser. No. 08/002,823, filed on Jan. 8, 1993, now abandoned.

BACKGROUND OF THE INVENTION

1. Field of the Invention

The invention relates to the field of chemical synthesis of oligonucleotides. More particularly, the invention relates to the synthesis of extremely high purity oligonucleotides.

2. Summary of the Related Art

Since the discovery by Zamecnik and Stephenson (*Proc. Natl. Acad. Sci.* 75, 280 (1978)) that synthetic oligonucleotides can inhibit Rous sarcoma virus replication, there has been great interest in the use of oligonucleotides and oligonucleotide analogs having modified internucleotide linkages to control gene regulation and to treat pathological conditions. There have been many reports of successful use of antisense oligonucleotides to inhibit gene expression both in vitro and in vivo, either directly by binding to double stranded DNA, or, primarily, indirectly by inhibiting translation of mRNA.

Many reports of successful antisense inhibition of nucleic acid expression in vitro have been reported. For example, Rapaport and Zamecnik (U.S. Pat. No. 5,616,564) disclosed successful antisense inhibition of malaria in parisitized erythrocytes. See also Barker et al. (*Proc. Natl. Acad. Sci. USA* 93, 514 (1996)). Oligodeoxyribonucleotide phosphorothioates have been found to inhibit immunodeficiency virus (Agrawal et al., *Proc. Natl. Acad. Sci. USA* 85, 7079 (1988); Agrawal et al., *Proc. Natl. Acad. Sci. USA* 86, 7790 (1989); Agrawal et al., in *Advanced Drug Delivery Reviews* 6, 251 (R. Juliano, Ed., Elsevier, Amsterdam, 1991); Agrawal et al. in *Prospects for Antisense Nucleic Acid Therapy of Cancer and AIDS*, 143 (E. Wickstrom, Ed., Wiley/Liss, New York, 1991); and Zamecnik and Agrawal in *Annual Review of AIDS Research*, 301 (Koff et al., Eds., Dekker, New York, 1991)), and influenza virus (Leiter et al., *Proc. Natl. Acad. Sci. USA* 87, 3420–3434 (1990)) in tissue culture. In addition, oligodeoxyribonucleotide phosphorothioates have been the focus of a wide variety of basic research (e.g., Agrawal et al., *Proc. Natl. Acad. Sci. USA* 87, 1401 (1990) and Eckstein and Gish, *Trends Biochem. Sci.* 14, 97 (1989)), enzyme inhibition studies (Mujumdar et al., *Biochemistry* 28, 1340 (1989)), regulation of oncogene expression (Reed et al., *Cancer Res.* 50, 6565 (1990)) and IL-1 expression (Manson et al., *Lymphokine Res.* 9, 35 (1990)) in tissue culture. A number of review articles report the many published studies of successful antisense inhibition in vitro. E.g., Uhlmann and Peyman, *Chem. Rev.* 90, 543 (1990).

A number of published reports disclose the successful antisense inhibition of nucleic acid expression in vivo. For example, Offensperger et al. (*EMBO J.* 12, 1257 (1993)) demonstrated in vivo inhibition of duck hepatitis B virus. Nesterova and Cho-Chung (*Nat. Med.* 1, 528 (1995)) demonstrated inhibition of tumor growth by a single subcutaneous injection of antisense phosphorothioate oligonucleotide targeted to the RI, subunit of protein kinase A in nude mice. Several general reviews of in vivo antisense inhibition have appeared that discuss these and other studies demonstrating successful in vivo antisense inhibition of nucleic acid expression as well as applications for therapeutic use. See, e.g., Agrawal, *TIBTECH* 14, 376 (1996); Field and Goodchild, *J. Exp. Opin. Invest. Drugs* 4, 799 (1995).

These and other studies have proven sufficiently successful to justify extension to humans. A number of human clinical trials are currently ongoing, testing antisense oligonucleotides against a variety of disease causing targets, including HIV, CMV retinitis, ICAM, PKC, c-myb, and c-raf.

A necessary precursor to using antisense oligonucleotides to inhibit nucleic acid expression is the synthesis of the oligonucleotides. Various methods have been developed for the synthesis of oligonucleotides for such purposes. Early synthetic approaches included phosphodiester and phosphotriester chemistries. Khorana et al. (*J. Molec. Biol.* 72, 209 (1972)) discloses phosphodiester chemistry for oligonucleotide synthesis. Reese (*Tetrahedron Lett.* 34, 3143 (1978)) discloses phosphotriester chemistry for synthesis of oligonucleotides and polynucleotides. These early approaches have largely given way to the more efficient phosphoramidite and H-phosphonate approaches to synthesis. Beaucage and Caruthers (*Tetrahedron Lett.* 22, 1859 (1981)) discloses the use of deoxynucleoside phosphoramidites in polynucleotide synthesis. Agrawal and Zamecnik (U.S. Pat. No. 5,149,798) discloses optimized synthesis of oligonucleotides by the H-phosphonate approach.

Both of these modem approaches have been used to synthesize oligonucleotides having a variety of modified internucleotide linkages. Agrawal and Goodchild (*Tetrahedron Lett.* 28, 3539 (1987)) teaches synthesis of oligonucleotide methylphosphonates using phosphoramidite chemistry. Connolly et al. (*Biochemistry* 23, 3443 (1984)) discloses synthesis of oligonucleotide phosphorothioates using phosphoramidite chemistry. Jager et al. (*Biochemistry* 27, 7237 (1988)) discloses synthesis of oligonucleotide phosphoramidates using phosphoramidite chemistry. Agrawal et al. (*Proc. Natl. Acad. Sci. USA* 85, 7079 (1988)) discloses synthesis of oligonucleotide phosphoramidates and phosphorothioates using H-phosphonate chemistry.

A number of treatises and review articles have appeared that discuss the various synthetic approaches. E.g., *Methods in Molecular Biology*, Vol. 20, *Protocols for Oligonucleotides and Analogs*, p. 63–80 (S. Agrawal, Ed., Humana Press 1993); *Methods in Molecular Biology*, Vol. 26: *Protocols for Oligonucleotide Conjugates* (Agrawal, Ed., Humana Press, Totowa, NJ 1994); *Oligonucleotides and Analogues: A Practical Approach* pp. 155–183 (Eckstein, Ed., IRL Press, Oxford 1991); *Antisense Res. and Applns.* pp. 375 (Crooke and Lebleu, Eds., CRC Press, Boca Raton, FL 1993); *Gene Regulation: Biology of Antisense RNA and DNA* (Erickson and Izant, eds., Raven Press, New York, 1992).

Both phosphoramidite and H-phosphonate chemical syntheses are carried out on a solid support that is stored in a reaction vessel. The required reaction steps for coupling each nucleotide are detritylation, coupling, capping, and oxidation. For small scale (up to 1 µmole) synthesis, the total time for the addition of one nucleotide is about 6 minutes. An oligonucleotide, 30-mer in length, can be assembled in 180 minutes. Under these conditions, synthesized oligonucleotides are chemically pure and biologically active. However, when oligonucleotides are synthesized on a larger scale (up to 1 mmole), the time for addition of each nucleotide onto CPG is in the range of 30 to 60 minutes, requiring approximately 12–25 hours for assembling a 25-mer oligonucleotide. The increase in time is due to the volume of the solid support being used in synthesis. This increase in cycle time exposes the already assembled oligonucleotide sequence to all reaction steps (including dichloroacetic acid detritylation step, coupling step, oxidation step and capping step) for a longer time. This increase in total assembly time affects the yield as well as chemical and biological properties of the compound. The chemical and biological properties are mainly affected by depurination, base modifications, and the like.

To reduce the effects of these problems, it is possible to synthesize oligonucleotides using dimeric or multimeric synthons, thereby reducing the number of cycles, and thus the time required for synthesizing oligonucleotides. To this end, several investigators have worked toward developing acceptable dimeric or multimeric synthon approaches. Khorana (*Science* 203, 614 (1979)) introduced the concept of multimeric synthons, using a phosphodiester approach. Crea and Itakura (*Proc. Natl. Acad. Sci. USA* 75, 5765 (1978)), Reese (*Tetrahedron Lett.* 34, 3143 (1978)), and Ohtsuka et al. (*Nucleic Acids Res.* 10, 6553 (1982)) all disclose use of dimeric or multimeric synthons in a phosphotriester approach. Kumar and Poonian (*J. Org. Chem.* 49, 4905 (1984)) and Wolter et al. (*Nucleosides and Nucleotides* 5, 65 (1986)) disclose synthesis of oligonucleotide phosphodiesters using dimeric phosphoramidite synthons. Marugg et al. (*Nucleic Acids Res.* 12, 9095 (1984)) teaches use of a dinucleotide thiophosphotriester to produce oligonucleotides containing one phosphorothioate linkage. Connolly et al. (*Biochemistry* 23, 3443 (1984)) and Cosstick and Eckstein (*Biochemistry* 24, 3630 (1985)) disclose addition of one dinucleotide phosphorothioate to a growing oligonucleotide chain using a phosphoramidite approach. Brill and Caruthers (*Tetrahedron Lett.* 28, 3205 (1987)) discloses synthesis of thymidine dinucleotide methylphosphonothioates. Roelen et al. (*Nucleic Acids Res.* 16, 7633 (1988)) discloses a solution phase approach, using a reagent obtained in situ by treating methylphosphonothioic dichloride with 1-hydroxy-6-trifluoromethyl benzotriazole to introduce a methylphosphonothioate internucleotide linkage into a dinucleotide in 60–70% yield, and produces a hexamer containing the linkage by two consecutive condensations of dimers. Roelen et al. (*Tetrahedron Lett.* 33, 2357 (1992)), discloses reagents for alkylphosphonate and alkylphosphonothioate chemistry. It discloses the solution phase synthesis of TG methyl, n-butyl, and n-octyl phosphonate and phosphonothioate dimers.

Leba dev et al. (*Tetrahedron. Lett.* 31, 855 (1990)) discloses a solution phase approach to produce dinucleotides containing a stereospecific methylphosphonothioate internucleotide linkage in 50–60% yield. Katti and Agarwal (*Tetrahedron Lett.* 27, 5327 (1986)) discloses 3' 1-methoxycarbonate methylphosphonate dimers.

The use of such synthons in the synthesis of oligonucleotides has also been disclosed. Kumar and Poonian, supra, demonstrated the use of 3' phosphoramidite methyl phosphotriester dimers in the solid phase manual synthesis of a 29-mer with an overall yield of 93.4%. Wolter, supra, demonstrated the automated, solid phase synthesis of a 101-mer using β-cyanoethyl-protected phosphoramidite dimers. Miura et al. (*Chem. Pharm. Bull.* 35, 833 (1987)) discloses automated solid-phase synthesis of pentadecathymidilate with phosphoramidite dimers. And Bannwarth (*Helv. Chim. Acta* 68, 1907 (1985) disclosed the use of phosphoramidite dinucleotides in the synthesis of oligonucleotides of modest length (N=8–11).

Krotz et al. recently reported the synthesis of phosphorothioate dimers having low phosphodiester dimer content. They used these dimers to synthesize phosphorothioate oligo(T) and oligo(TC) nucleotides, wherein they observed that the N/N−1 ratio was on the order of 99:1 as measured by capillary gel electrophoresis (CGE). The phosphodiester content of the oligomers was on the order of 1% as determined by $^{31}P$ NMR for oligomers synthesized with phosphorothioate dimers wherein the phosphorothioate linkage is protected by a β-cyanoethyl group on the non-bridging oxygen. A similar reduction of the phosphodiester content was not observed for dimers wherein the phosphorothioate linkage was protected by a β-cyanoethyl group on the (non-linking) sulfur.

Once synthesized, the desired oligonucleotide (being "N" nucleotides in length) must be isolated from failure sequences (i.e., sequences with fewer than "N" nucleotides, such as N−1, N−2, etc.) and other impurities. While automated synthesizers have proven an invaluable tool for obtaining oligonucleotides, 1–3% of the reactions fail during each cycle in which a nucleotide monomer is to be added. Consequently, the resulting products are generally a heterogenous mixture of oligonucleotides of varying length. For example, in a typical 20mer synthesis, the 20mer product represents only 50–80% of the recovered oligonucleotide product.

Furthermore, preparation of oligodeoxynucleotides on a solid phase support requires that the oligodeoxynucleotide be cleaved from the support. Cleavage of the oligonucleotide from the support is typically accomplished by treating the solid phase with concentrated ammonium hydroxide. The ammonium hydroxide is conventionally removed under reduced pressure using, for example, a rotary evaporator. This method for removing the ammonium hydroxide, however, is not ideal for use in large scale isolation of oligodeoxynucleotides.

For most purposes (e.g., therapeutic or diagnostic) the purity of the compounds is extremely important. Consequently, there has been an interest in developing chromatographic techniques for purifying oligonucleotides. Because of their therapeutic potential, much of the focus has been on purifying oligonucleotide phosphorothioates.

Conventional methods for purifying oligodeoxynucleotides employ reverse-phase liquid chromatography. Manufacturing facilities using such methods require explosion-proof equipment because acetonitrile is typically used in the elution buffer.

Methods of oligodeoxynucleotide phosphorothioate purification have been published. Metelev and Agrawal (*Anal. Biochem.* 200, 342 (1992)) reported the ion-exchange HPLC analysis of oligodeoxyribonucleotide phosphorothioates on a weak anion-exchange column (Partisphere WAX) in which the weak anion exchanger utilizes a dimethylaminopropyl functional group bonded to Partisphere silica. This medium, with an ion-exchange capacity of 0.18 meq/g, exhibits an interaction with anions weaker than those observed with strong anion-exchange media. The authors of this study found that separation was length dependent for oligonucleotide phosphorothioates up to 25 nucleotides in length. Furthermore, N−1 peaks were separated from the parent peak. They also found that 30-mer and 35-mer oligonucleotide phosphorothioates were separable with the same gradient, although better separation could be obtained with a shallower gradient.

Metelev et al. (*Ann. N.Y Acad. Sci.* 660, 321–323 (1992)) reported the analysis of oligoribonucleotides and chimeric oligoribo-oligodeoxyribonucleotides using ion-exchange HPLC. They found that the retention time of the oligonucleotides studied depended on the number of ribonucleotide moieties in the oligonucleotide. In addition, the retention time of oligoribonucleotides was found to be length dependent. The authors noted that oligoribonucleotides of length up to 25 nucleotides could be purified and analyzed.

Bigelow et al. (*J. Chromatography* 533, 131 (1990)) reported the use of ion-pair HPLC to analyze oligonucleotide phosphorothioates. Stec. et al. (*J. Chromatography* 326, 263 (1985)) and Agrawal and Zamecnik (*Nucleic Acids Res.* 19, 5419 (1990)), reported HPLC analysis of oligodeoxyribonucleotides containing one or two phosphorothioate internucleotide linkages using a reversed-phase column.

Tang et al. (WO 95/27718) disclosed a purification techniques suitable for large scale separation of oligonucleotide phosphorothioates. The method uses DMAE Fractogel EMD column with an organic solvent-free, low salt, elution buffer. The method does not require elevated temperatures, making it more amenable for large scale chromatography.

Puma et al. (WO 96/01268) disclosed a purification method not requiring the removal of ammonium hydroxide or the use of conventional C-18 silica gel reverse-phase liquid chromatography. The disclosed methods use hydrophobic interaction chromatography and DEAE-5PW anion ion-exchange chromatography.

As antisense oligonucleotides proceed through human clinical trials, there is an ever-increasing demand for extremely pure oligonucleotides in large quantities. Regulatory agencies around the world are addressing the requisite standards for antisense oligonucleotides as drug compounds. E.g., Kambhampati et al, *Antisense Res. Dev.* 3, 405 (1993). Consequently, there remains a need for new methods of producing large quantities of highly pure oligonucleotides.

SUMMARY OF THE INVENTION

The invention provides new methods for producing dimeric nucleotide synthons, hereafter called "dimer blocks," having modified internucleotide linkages, e.g,. alkylphosphonate, phosphoramidate, phosphorothioate, or alkylphosphonothioate. Phosphorothioates are the preferred modified internucleotide linkage. According to this aspect of the invention, synthesis of dimer blocks proceeds in a single pot solution phase reaction, regardless of the type of internucleotide linkage in the dimer block. For example, to synthesize dimer block alkylphosphonates, condensation of a nucleoside 3'-alkylphosphonamidite with a 3'-protected nucleoside is carried out. For synthesis of dimer block phosphoramidates, alkylamine is added after H-phosphonate condensation of nucleotides. For synthesis of dimer block phosphorothioates, sulfurization using an appropriate sulfur reagent follows solution phase coupling of the protected monomeric nucleotides to yield a dimer. For preparing dimer block alkylphosphonothioates, an alkylphosphonamidite is used in the same one pot reaction as described for dimer block phosphorothioates. This simple chemistry allows for the synthesis of all possible dimer block methylphosphonothioates and promotes preparation of dimer blocks having 3'-condensing groups.

Thus, in a second aspect the invention provides novel dimer blocks comprising the nucleotides GG, GA, GT, GC, AG, AA, AT, AC, TG, TA TC, TT, CG, CA, CT or CC linked together by alkylphosphonate, phosphoramidate, phosphorothioate or alkylphosphonothioate linkages, and having various combinations of protective groups and condensing groups. These dimer blocks also give rise to a method of using such dimer blocks to assemble oligonucleotides containing alkylphosphonate, phosphoramidate, phosphorothioate, or alkylphosphonothioate linkages. Moreover, the dimer blocks allow assembly of oligonucleotides having exclusively alkylphosphonate, phosphoramidate, phosphorothioate or alkylphosphonothioate internucleotide linkages, or mixtures thereof.

Thus, in a third aspect, the invention provides methods of using dimer blocks to assemble oligonucleotides having alkylphosphonate, phosphorothioate, phosphoramidate or alkylphosphonothioate linkages or having combinations of two or more of these. It is an object of the invention to provide efficient methods that reduce total assembly time of oligonucleotides. It is a further object of the invention to provide efficient methods that reduce total solvent consumption required for oligonucleotide assembly. It is also an object of the invention to provide efficient methods that ease purification of oligonucleotides by increasing the yield of full length oligonucleotides. It is an additional object of the invention to provide efficient methods that reduce side reactions by reducing the exposure of partially assembled oligonucleotides to chemicals. It is also an object of this aspect of the invention to provide highly pure dimers that facilitate synthesis and purification of extremely highly pure oligonucleotides. Finally, it is an object of the invention to reduce overall cost of oligonucleotide assembly by allowing the use of inexpensive solution phase chemistry to achieve half of the total synthesis.

The present invention also provides oligonucleotides and methods for synthesizing them with a heretofore unobtainable purity. In one aspect, the invention provides a population of oligonucleotides having a purity of greater than 98%. In one embodiment of this aspect of the invention, oligonucleotides are provided that have an N–1 content of less than 2%, preferably less than 1%, and more preferably less than 0.5% of the content of the desired oligonucleotide (the N oligonucleotide).

In one embodiment, the present invention comprises a population of oligonucleotides having all phosphorothioate internucleoside linkages, wherein the amount of phosphodiester impurity at each of the phosphorothioate linkages is less than 1%, preferably less than 0. 1%, and most preferably undetectable, by $^{31}$P NMR.

The extremely high purity of oligonucleotides according to the invention sets a new industry standard.

In another aspect, the present invention comprises a method for large scale ($\geq$ca. 100 $\mu$mol) synthesis of oligonucleotides of extremely high purity. The method comprises synthesizing oligonucleotides using nucleotide dimers (herein called "dimer blocks") in place of mononucleotides as the basic synthetic unit. In the method of the present invention, oligonucleotide populations with extremely high purity are obtained.

In another embodiment of this aspect of the invention, synthesis is conducted using standard techniques except that dimer blocks are used and the normal capping step is eliminated. We have found that excellent results (i.e., high yields of high purity oligonucleotide) can be obtained without the usual capping step.

In another embodiment of this aspect of the invention, synthesis by either of the two previous embodiments is conducted using about six or less equivalents of dimer per coupling. Preferably, four equivalents and most preferably two equivalents of dimer are used per coupling step.

The inventive method provides extremely high purity oligonucleotides with both a savings in cost of production as well as time. The oligonucleotides produced by the inventive method are ideally suited for in vivo therapeutic methods of treatment.

The foregoing merely summarizes certain aspects of the present invention and is not intended, nor should it be construed as limiting the invention in any way. All patents and other publications recited herein are hereby incorporated by reference in their entirety.

DETAILED DESCRIPTION OF THE INVENTION

The invention relates to reagents and methods for assembling oligonucleotides. More particularly, the invention relates to the assembly of oligonucleotides having modified internucleotide linkages.

Synthesis of Dimer Blocks

In a first aspect, the invention provides new processes for making dimer blocks. Dimer blocks are dimeric nucleotides having modified internucleotide linkages and blocking groups at the 5'-hydroxyl. Preferred blocking groups include tert-butyldimethylsilyl, dimethoxytrityl, levulinyl, monomethoxytrityl and trityl groups. The 3' position of the dimer block may have a blocking group, a free hydroxyl, or a β-cyanoethylphosphoramidite group. Preferred modified internucleotide linkages include phosphorothioate, alkylphosphonate and alkylphosphonothioate linkages. The modified linkage of the dimer block has an alkoxy or alkyl group.

In a very general sense, the method of synthesizing dimer blocks according to the invention can be considered to be a method of synthesizing a dimer block having an alkylphosphonate, phosphoramidate, phosphorothioate or alkylphosphonothioate internucleotide linkage, the method comprising the steps of:

(a) condensing together a first nucleoside derivative having a protective group at a 5' end and a condensing group at a 3' end with a second nucleoside derivative having a protective group at a 3' end and a hydroxyl group at a 5' end to form a dinucleotide derivative having a reduced internucleotide linkage, and (b) oxidizing the internucleotide linkage with an appropriate oxidizing agent to yield a dimer block alkylphosphonate, phosphoramidate, phosphorothioate or alkylphosphonothioate.

The precise dimer block obtained, of course will depend upon the nature of the first nucleoside derivative and the oxidizing agent, as shown in Table 1:

TABLE 1

| Dimer Block Type | First Nucleoside Derivative | Oxidizing Agent |
| --- | --- | --- |
| alkylphosphonate | nucleoside-3'-alkyl N,N di-isopropyl phosphonamidite | iodine |
| phosphoramidate | nucleoside-3'-H phosphonate | alkyl- or arylamine |
| phosphorothioate | nucleoside-3'-O-alkyl N,N, diisopropyl phosphoramidite | sulfurizing reagent |
| alkylphosphono-thioates | nucleoside-3'-alkyl N,N diisopropyl phosphonamidite | sulfurizing reagent |

In a first embodiment of this aspect of the invention, the method produces a dimer block having 5' and 3' blocking groups and a phosphorothioate internucleotide linkage. In this embodiment, the method comprises the steps of (a) joining together, by phosphoramidite chemistry, a nucleoside having a 5' blocking group and a nucleoside having a 3' blocking group, and (b) adding an appropriate sulfurizing agent, such as the Beaucage reagent. The Beaucage reagent (3H-1,2-benzodithiol-3-one-1,1-dioxide) is taught in U.S. Pat. No. 5,003,097.

Examples of the preferred method of synthesizing phosphorothioate dimers are given below. We have found that synthesis of phosphorothioate dimers by this method results in a population of phosphorothioate dimers having very low phosphodiester dimer impurity. The use of these phosphorothioate dimer blocks in the synthesis of oligonucleotides in turn results in phosphorothioate oligonucleotides with less phosphodiester impurity.

In a second embodiment of this aspect of the invention, the method produces a dimer block having a 5' blocking group, a 3' free hydroxyl group, and a phosphorothioate internucleotide linkage. In this embodiment, the method comprises steps (a) and (b) of the first embodiment above, and further comprises the step of (c) deprotecting the 3'-hydroxyl group. This is achieved by the use of conditions selective for removal of the 3' protective group only. For example, if the 5' protective group is dimethoxytrityl, monomethoxytrityl or trityl, and the 3' group is tert-butyldimethylsilyl, then selective removal of the 3' group is obtained by treatment with tetrabutylammonium fluoride. Alternatively, if the 5' group is dimethoxytrityl, monomethoxytrityl or trityl and the 3' group is levulinyl, selective removal of the 3' group is obtained by treatment with hydrazine monohydrate in pyridine/acetic acid.

In a fourth embodiment of this aspect of the invention, the method produces a dimer block having a 5' blocking group, a 3' β-cyanoethyl phosphoramidite group and a phosphorothioate internucleotide linkage. In this embodiment the method comprises steps (a), (b) and (c) of the first two embodiments described above, and further comprises the step of (d) converting the free 3' hydroxyl group to a 13-cyanoethyl phosphoramidite group.

Those skilled in the art will recognize that as an alternative to the third and fourth embodiments, dimer blocks having phosphotriester 3' groups can be prepared according to well known procedures.

In additional embodiments of this aspect of the invention the method produces dimer blocks having a 5' blocking group, an alkylphosphonothioate, alkylphosphonate or phosphoramidate internucleotide linkage, and a 3' group that may be a blocking group, a free hydroxyl, a β-cyanoethyl phosphoramidite group, or a phosphotriester group. In these embodiments, the method is carried out exactly as described for the four embodiments above to produce dimer block alkyl-phosphonothioates, except that the starting material is a nucleoside alkylphosphonamidite. Analogous dimer block alkylphosphonates are prepared in identical fashion to the dimer block alkylphosphonothioates, except that an iodine solution is used in place of the sulfurizing agent. Analogous dimer block phosphoramidates are prepared by H-phosphonate condensation followed by oxidation of the linkage with an alkyl- or arylamine in carbon tetrachloride.

This first aspect of the invention offers a method of producing dimer block products that are useful as intermediates for assembling oligonucleotides having modified internucleotide linkages. The ability to produce these dimer blocks in a one pot reactions greatly simplifies their production.

Dimer Blocks

In a second aspect, the invention provides novel dimer block products having a 5' blocking group, a modified internucleotide linkage and a 3' group that may be a blocking group, a free hydroxyl, an H-phosphonate group, or in some cases a β-cyanoethyl phosphoramidite. The method for producing these dimer blocks is independent of the sequence of the nucleotides in the dimer block, thus allowing production of all possible dimer sequences containing alkylphosphonate, phosphoramidate, phosphorothioate or alkylphosphonothioate linkages, i.e., GG, GA, GT, GC, AG, AA, AT, AC, TG, TA, TT, TC, CG, CA, CT, and CC. Such dimers are illustrated below:

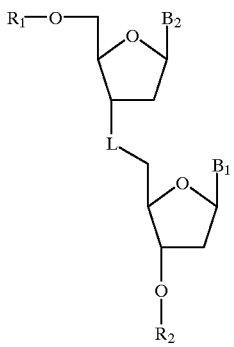

Where $B_1$ and $B_2$ are the same or different nucleotide base (e.g., G, A, T, C, or modifications thereof, and $R_1$ is a protective group such as dimethoxytrityl, monomethoxytrityl or trityl, L is an alkylphosphonate, phosphoramidate, thiophosphotriester, or alkylphosphonothioate, and $R_2$ is an H, a β-cyanoethylphosphoramidite, or a protective group such as levulinyl or t-butyldimethylsilyl. Although the foregoing illustrates DNA/DNA dimers, RNA/RNA, RNA/DNA, and DNA/RNA dimers are also encompassed within the scope of the invention disclosed herein.

Synthesis of Ultra-pure Oligonucleotides Using Dimer Blocks

In a third aspect, the invention provides a method of using dimer blocks to assemble oligonucleotides having modified internucleotide linkages. In this aspect, dimer blocks having modified internuclcotide linkages (e.g., phosphorothioate, alkylphosphonate, phosphoramidate, or alkylphosphonothioate), are used to assemble oligonucleotides having such modified internucleotide linkages (dimer blocks having 5' blocking groups and 3' β-cyanoethyl phosphoramidite are used). Synthesis is then conducted according to the phosphoramidite approach by condensing the dimer block with the nascent oligonucleotide. (As used herein, the term "nascent oligonucleotide" means the less-than-full-length, solid support-bound synthetic nucleic acid that upon elongation results in the desired synthetic oligonucleotide.) Support of oligonucleotide synthesis with dimer blocks can be, for example, soluble polymers as well as insoluble CPG and polymer beads.

In order to ensure obtaining oligonucleotides of extremely high purity as disclosed herein, it will be appreciated that measures should be taken at each step in the synthetic/purification process to maximize the purity. According to the present invention, this begins with using dimers as the elemental oligonucleotide building block. In the synthetic methods disclosed herein, dimer phosphoramidites are used. Preferably the dimer phosphoramidite is at least 90% pure (as determined by HPLC). More preferably it is at least 96% pure. Most preferably it is at least 98% pure.

In the phosphoramidite approach, β-cyanoethyl tetraisopropylphosphorodiamidite and tetrazole are used to activate a 5'-DMT, β-cyanoethyl protected dimer to yield the phosphoramidite dimer, such as depicted in the following in which a phosphorothioate dimer is illustrated:

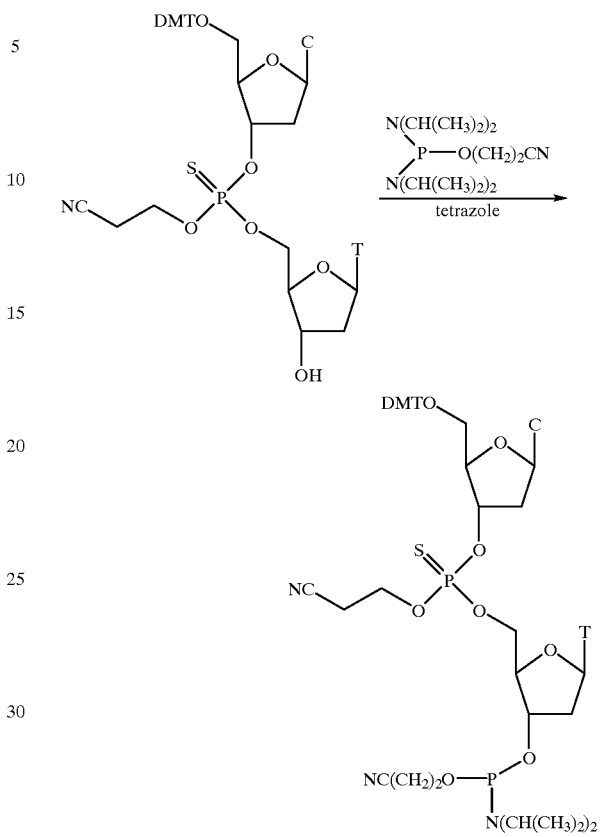

Alternatively, 2-cyanoethyl diisopropylchlorophosphoramidite can be used instead of the diamidite displayed in the scheme above.

Three principal types of impurities generally arise in this reaction. The first results from hydrolysis of the dimer amidite to yield an H-phosphonate dimer. The second impurity is the starting material itself, the 3'-hydroxy dimer. Both of these impurities are "inert" in the sense that they will not react with the nascent oligonucleotide and contribute to the N−x or N+x content of the final oligonucleotide product (where N is the number of nucleotides in the final, full-length oligonucleotide and x is an integer ≧1).

The third principal type of impurity is the tetrazole-activated phosphorodiamidite. This impurity is not inert and measures should be taken to minimize its presence. Preferably, the tetrazole and dimer are first combined and then added together to the diamidite under conditions in which the tetrazole is not in great excess of the diamidite. This results in a low probability that two molecules of tetrazole will react with the diamidite. Preferably, the tetrazole and diamidite are used in ~1:1 ratio and each in slight excess of the dimer. A suitable amount of each is 1.3 cq diamidite and 1.2 eq tetrazole per eq of dimer. After the reaction is complete, the product is preferably washed several times as described in the synthesis of dimer 24 in Example 4, below. Following the foregoing protocol minimizes the amount of non-inert impurity.

An advantage of the present method is that oligonucleotide synthesis can be conducted on commercially available synthesizers using standard cycles, substituting dimers for the usual monomers. This is demonstrated, for example, in Example 6–9, below.

Following synthesis, the oligonucleotide product is cleaved from the solid support and subject to purification by Ion-Exchange Chromatography (IEX). Optionally, the oligonucleotide can first be purified by Reverse Phase Chromatography (RPC) before IEX. As described by Puma et al. (WO 96/01268), Hydrophobic Interaction Chromatography (HIC) can be useful as the initial chromatographic step. For the purposes of the present invention, however, RPC is preferred. Advantageously, standard protocols of purifying oligonucleotides by these techniques can be employed. Although High Pressure Liquid Chromatography (HPLC) can also be used, the present method offers the additional advantage of using Medium Pressure Liquid Chromatography (MPLC), which is preferable because it is cheaper and more easily adaptable to large scale synthesis.

To obtain the high purity levels as disclosed herein, careful screening and pooling of chromatography fractions is preferable. Screening of fractions and/or trial pools of fractions is preferably conducted by analytical Capillary Electrophoresis (CE) to determine the degree of purity and yield of each fraction. Then, fractions having an acceptable degree of purity and yield are pooled in a pre-determined manner to yield a final population of oligonucleotides having a sufficiently high degree of purity and yield. Depending on the application, one may be willing to sacrifice some yield to obtain a higher degree of purity, and vice versa. Such pooling methods are well known to those skilled in the art.

Following this general protocol results in oligonucleotides of heretofore unrealized purity, as demonstrated in the Examples below. The degree of purity obtainable according to the methods of this aspect of the invention is described in detail below.

In addition, we have surprisingly found that synthesis of ultra-pure oligonucleotides according to this aspect of the invention can be conducted without compromising purity or yield using an amount of dimer block that is much less than has previously been thought possible. Prior art methods, such as those disclosed by Wolter et al., supra, have used a large excess of dimer (often in the range of tens of equivalents) in order to drive the reaction to completion and ensure high yield. We have surprisingly found, however, that fewer than about 6 equivalents can be used and still obtain high yields of highly pure oligonucleotide. Accordingly, in a preferred embodiment of this aspect of the invention, ≦6 equivalents of dimer are used in each coupling step. More preferably ~2 equivalents of dimer are used per coupling step.

Traditional methods of synthesis, be it using monomers or dimers, employ a capping step during each synthetic cycle to block unreacted reactive sites, thereby minimizing subsequent addition of nucleotides to these sites rather than to the nascent oligonucleotide. Capping was thought to be a necessary step to achieve high yields of pure oligonucleotides. We have surprisingly found, however, that synthesis of oligonucleotides using dimer blocks as disclosed herein can be conducted without the capping step. The elimination of the capping step also results in a tremendous savings in time and money without sacrificing yield.

Accordingly, in another preferred embodiment of this aspect of the invention, dimer block synthesis of oligonucleotides is conducted without the capping step.

Purification of oligonucleotides prepared by dimer block synthesis may be accomplished using two approaches. When the purity of the crude oligonucleotide is relatively low, the crude oligonucleotide is preferably purified by RPC followed by IEX. Oligonucleotides having a N:N−1 ration of 100:0 (i.e., non-detectable amounts of N−1 oligonucleotide) can be obtained.

Alternatively, for crude products of higher purity, RPC can be omitted and the crude oligonucleotide purified by IEX to give an oligonucleotide with an N:N−1 ratio of 100:0 (i.e., no detectable N−1 impurity).

As evidenced in Table 5, crude products having a range of purities have been obtained. Depending on the purity of the crude product, a two-step chromatographic purification (RPC followed by IEX) or a single-step chromatographic purification (IEX only) may be employed. As evidenced in Table 4, crude products of lower purity (e.g., 15 and 300 μmol scale, synthesized with capping) are purified by RPC to yield an intermediate material whose purity is approximately equivalent to that of a crude product having high purity as originally synthesized (e.g., 300 μmol scale, synthesized without capping). In the current comparison, relative purities of crude products are clearly differentiated on the basis of IEX and CE analyses. Relative purities of feedstocks taken for purification by IEX are well defined by IEX analysis of the detritylation mixtures.

As evidenced in Table 4, the single-step chromatographic purification provides higher overall recoveries. Taken together, the two approaches (i.e., the one step and two step approaches) provide robust and versatile tools for purification of oligonucleotide prepared by dimer synthesis. Crude products having a range of purities can be accommodated.

A strongly preferred technique in achieving required purity is rigorous screening of trial pools by CE analysis. During initial work at 15 μmol scale (infra), this technique was not employed. In that work, product purity was 97% by CE and (N+x) content was 2.4%. In subsequent work, rigorous use of CE analysis was incorporated and product purities≧98% by CE were achieved, and (N+x) content was reduced to 0.3% or less.

The data indicate that dimer synthesis, performed with or without capping, provides a crude product which can be brought to≧98% final purity. Achievement of 98+% product purity can be seen as arising from the following factors:

(1) Use of dimer synthesis. This approach has the inherent potential to entirely eliminate (N−1) impurity. Such impurity presents the greatest challenge to chromatographic purification.

(2) Use of high-resolution preparative chromatography.

(3) Rigorous use of capillary electrophoresis to analyze trial pools prepared from chromatographic fractions.

The synthetic methods of the invention can be conducted at both small (e.g., 1 μmol) scale as well as large (e.g., ≧100 μmol) scale, resulting in oligonucleotide product with similar purity and yield.

In any of the embodiments according to this aspect of the invention, both monomers of any dimer block used in the synthetic method can be deoxyribonucleotides, or one can be a deoxyribonucleotide and the other can be a ribonucleotide.

In a preferred embodiment of the present method, dimer phosphorothioates are employed to yield an oligonucleotide comprising entirely phosphorothioate internucleoside linkages. Oligonucleotide phosphorothioates with a PO impurity level of less than 0.5%, preferably 0.3%, more preferably ≦0.4%, and most preferably non-detectable by $^{31}$P NMR can be obtained.

In a preferred embodiment, the purity of the crude oligonucleotide phosphorothioate (i.e., before purification by chromatographic means) produced by the method according to the invention is ≧75% as determined by CE. Preferably in this embodiment:

a) the N−1 content is non-detectable;
b) the N−1 content is non-detectable, the N−2 content is <6%, the N−x content for x>2 is ≦15% and the PO content is ≦0.6%;
c) the N−1 content is non-detectable and the N−2 content is <1%;
d) the N−1 content is <2%;
e) the N−1 content is less than or equal to 0.5%; or
f) the N+x content is <8%.

Another preferred dimer block is one having a phosphotriester internucleotide linkage.

Those skilled in the art will recognize that this approach also allows the convenient synthesis of mixed phosphate backbone oligonucleotides, e.g., oligonucleotides having any combination of one or more phosphorothioate, alkyl-/arylphosphonothioate, phosphodiester, and/or alkyl-/arylphosphonate linkages.

The method according to this aspect of the invention provides several advantages over monomeric synthesis of oligonucleotides. First, since half as many assembly cycles are required, the total assembly time is reduced by half, which, for large scale synthesis, can be a saving of 12 hours or more for a single oligonucleotide. This reduction in time also results in fewer side reactions, since partially assembled oligonucleotides are exposed to chemicals for a shorter time. The method also facilitates purification of oligonucleotides by increasing the proportion of full length oligonucleotides, since that proportion varies inversely with the number of cycles performed. Finally, the method reduces cost of synthesis by cutting solvent consumption by half and by allowing one half of the total synthesis to be carried out using inexpensive solution phase chemistry. The present method extends these advantages to oligonucleotides having exclusively phosphorothioate, alkylphosphonate, phosphoramidate, or alkylphosphonothioate linkages as well as to oligonucleotides having any combination thereof.

Ultra-Pure Oligonucleotides

The methods of the third aspect of the invention produce oligonucleotides of heretofore unobtainable purity. Accordingly, in a fourth aspect, the invention provides oligonucleotides produced by the methods of the third aspect of the invention and having a purity described below. Oligonucleotide phosphorothioates are a preferred oligonucleotide according to this aspect of the invention. As used herein, the term oligonucleotide phosphorothioate is an oligonucleotide having all phosphorothioate internucleotide linkages.

Oligonucleotide product of length N contains two major types of impurities, size impurity (type "A") and composition impurity (type "B") such that the "total purity" of a population of oligonucleotides can be defined by:

$$\text{total purity} = 100\% - (\% \text{ impurity } A + \% \text{ impurity } B)$$

where "% impurity A" is the total percentage of oligonucleotides of length other than N (i.e., % (N+x)+% (N−x), where x is an integer other than 0 and N+x represents all oligonucleotides of length greater than N nucleotides and N−x represents all oligonucleotides of length less than N nucleotides). Type A impurities are detectable and quantitatable by capillary electrophoresis.

"% impurity B" relates to oligonucleotides having all modified (i.e., non-phosphodiester) linkages and is the total percentage of oligonucleotides of length N having one or more phosphodiester internucleotide linkages in place of the modified linkage. In the preferred oligonucleotide phosphorothioates, the type B impurity is an oligonucleotide having at least one phosphorothioate linkage replaced by a phosphodiester linkage. Type B impurities (commonly called "PO" impurities) are detectable along with N−x' impurity by ion exchange chromatographic (IEX) analysis of oligonucleotide (DMT-off form). The peak in the IEX chromatogram corresponding to the PO impurity plus the N−x' impurity appears just before the peak of the desired N-mer oligonucleotide. With reference to this impurity peak, the term N−x' refers to the sum of N−2 plus N−3 and/or N−4. (The terms N−2, N−3, and N−4 as employed in this calculation are defined further below.) As defined, the type B (or PO) impurity is estimated for oligonucleotides by using the following formula:

$$\%PO = [\alpha_{PO/N-x'}]_{IEX}[\alpha_{N-2}+\alpha_{N-3,4}]_{CE}$$

where $$\alpha_i = \frac{A_i}{\sum_j A_j} \times 100\%$$

and $A_i$ is the area under peak "i" of the chromatogram, the sum in the denominator of the definition of "α" is over all peaks in the chromatogram, and the subscripts "IEX" and "CE" indicate the chromatographic technique from which the data were obtained. $\alpha_{PO/N-x}$ refers to the peak immediately preceding the peak corresponding to the "N" oligomer in IEX and has contributions from both N−x oligonucleotides and N oligonucleotides having a PO internucleoside linkage. $[\alpha_{N-2}]_{CE}$ corresponds to oligonucleotides of length N−2, and $[\alpha_{N-3,4}]_{CE}$ corresponds to the peak immediately preceding the N−2 peak in CE chromatograms and is believed to arise primarily from oligonucleotides of length N−3 and/or N−4. The above formula for calculating estimated values for %PO was applied only to product purified by IEX (DMT-off). Results appear in Table 4. A second approach was applied to calculating estimated values for %PO in crude oligonucleotides (DMT-on):

$$\% PO = \frac{[A_{PO/N-x'}]_{IEX} / [A_{PO/N-x'} + A_N]_{IEX}}{N-1} \times 100.$$

Wherein $[A_{PO/N-x'}]_{IEX}$ refers to the area of the peak immediately preceding that corresponding to the DMT-on form of the N oligonucleotide. This calculation tends to overestimate the PO content as it does not subtract the contribution from N−x' impurities. Thus, this approach provides a conservative estimate of purity with respect to PO content. Values based on this calculation appear in Table 5. For both pure and crude oligonucleotide, %PO can also be determined by $^{31}P$.

Other calculations employed herein are based on the PO/N−x' peak. %DMT-on (by IEX) is calculated as follows:

$$\%DMT\text{-}on = [\alpha_N + \alpha_{PO/N-x'}]_{IEX\text{-}DMT\text{-}n}$$

where $\alpha_{PO/N-x'}$ refers to the peak immediately preceding that for the DMT-on form of the N oligonucleotide. The calculation provides a useful estimate of combined phosphorothioate and phosphodiester forms of DMT-on oligonucleotide, N-oligomer. No correction is made for N−x' content in the $\alpha_{PO/N-x'}$ peak. Results based on this calculation appear in Tables 4 and 5.

In a preferred embodiment, oligonucleotide phosphorothioates according to this aspect of the invention have a total purity of 98% or more. More preferably, the total purity is greater than 99%. Preferably in these embodiments a) the N−1 content is non-detectable;
b) the N−1 content is non-detectable, the N−2 content is less than 1%, and the N−x content for x>2 is less than 2%;
c) the N−1 content is non-detectable and the N−2 content is less than 1%;
d) the N−1 content is non-detectable and the N−x content for x>1 is less than 2%;
e) the N−1 content is <2%
f) the N−1 content is less than or equal to 0.5%;
g) the N+x content is <2%;
h) the N+x content is <1%; or
i) the N+x content is <0.5%.

Unless expressly indicated otherwise, all percentages of oligonucleotides of a particular length mean percentages as measured by capillary gel electrophoresis. As used herein, "non-detectable" mean non-detectable by capillary gel electrophoresis, which can detect a single oligonucleotide size impurity (e.g., N−x and N+x) down to 0.15%. Typically in capillary electrophoresis, the noise level is ~20–30 mV. The minimum detectable peak has a S/N of ~3:1, or about 60 mV.

Oligonucleotides according to this aspect of the invention can be of essentially any conventionally synthesizable length and can be made according to the third aspect of the invention. Preferably, oligonucleotides according to this aspect of the invention are 50 or fewer nucleotides in length, more preferably, 30 or fewer, and most preferably of length of from about 15 to about 30 nucleotides.

In yet another embodiment of this aspect of the invention, the oligonucleotide phosphorothioates have less than 0.5% phosphodiester content (i.e., the number of phosphodiester linkages comprises less than 0.5% of the number of phosphorothioate linkages as measured by $^{31}$P NMR). Preferably, the PO content is less than or equal to 0.3%. More preferably, the phosphodiester content is less than or equal to 0.03%–0.04%, the lower limit of detection of $^{31}$P NMR. Even more preferably, the PO content is non-detectable by $^{31}$P NMR.

The following examples are intended to further illustrate certain preferred embodiments of the methods according to the invention, and are not intended to be limiting in nature.

EXAMPLES

Example 1

Solution Phase Synthesis Of 5'-O-dimethoxytrityl-thymidine-3'-O-methyl phosphorothioate-5'-O-N$^4$-benzoyl-2'-deoxycytidine The synthesis steps for this protected dimer block for synthesis of phosphorothioate containing oligonucleotides are shown below:

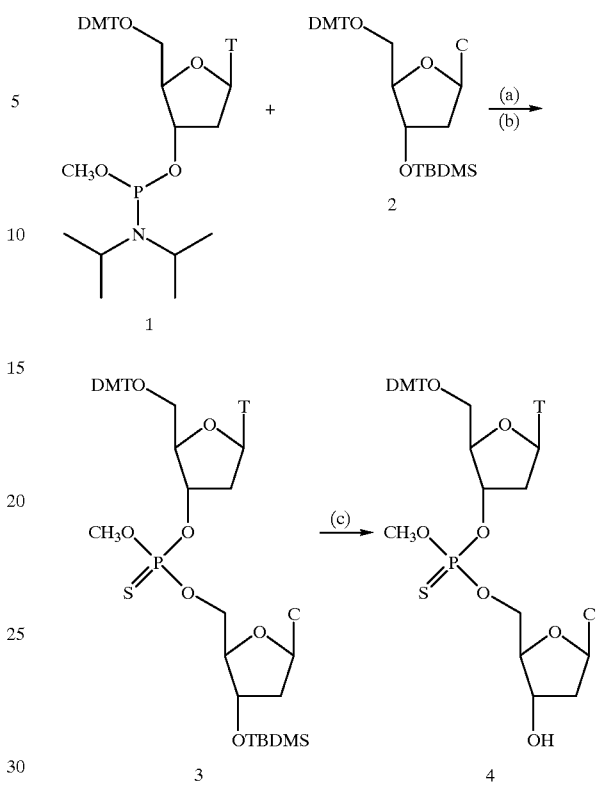

wherein (a) is anhydrous acetonitrile and tetrazole, (b) is Beaucage reagent, (c) is tetrahydrofuran and tetrabutyl ammonium fluoride, and DMT is dimethoxytrityl and TBDMS is tert-butyldimethylsilyl.

A mixture of 5'-O-dimethoxytrityl-thymidine-3'-O-methyl N,N-diisopropyl phosphoramidite, 1, (1.4 g, 2 mmol) and N$^4$-benzoyl-3'-O(tert-butyldimethylsilyl)-2'-deoxycytidine, 2, (0.88g, 2 mmol) was dissolved in anhydrous acetonitrile (25 ml) and a solution of tetrazole (0.45 M, 10 ml) was added. The reaction mixture was stirred at room temperature for 15 min. Beaucage reagent (0.6 g in anhydrous acetonitrile 15 ml) was added and the mixture was further stirred for 15 min. The reaction mixture was evaporated to remove most of the acetonitrile under reduced pressure. The crude reaction product was extracted with dichloromethane and washed with brine. The organic layer was dried over Na$_2$SO$_4$ and evaporated to dryness to obtain 3. Product 3 was re-dissolved in tetrahydrofuran (16 ml) and treated with a 1 M solution of tetrabutylammonium fluoride (3 ml, THF) for 15 min. The reaction mixture was evaporated to almost dryness and partitioned between dichloromethane and water. The organic layer was dried over Na$_2$SO$_4$ and evaporated to a small volume. The product was purified by column chromatography using silica gel (2.5×20 cm). The dimer block product, 4, was eluted with 0–7% methanol in dichloromethane (0.5% pyridine); obtain 1.3 g (70% yield); not optimized.

$^{31}$P NMR=70.06.

Example 2

Solution Phase Synthesis Of 5'-O-dimethoxytrityl-N$^4$-benzoyl-2'-deoxycylidine-3'-O-methyl phosphorothioate-5'-O-thymidine The synthesis steps for this dimer block for synthesis of phosphorothioate-containing oligonucleotides are shown below:

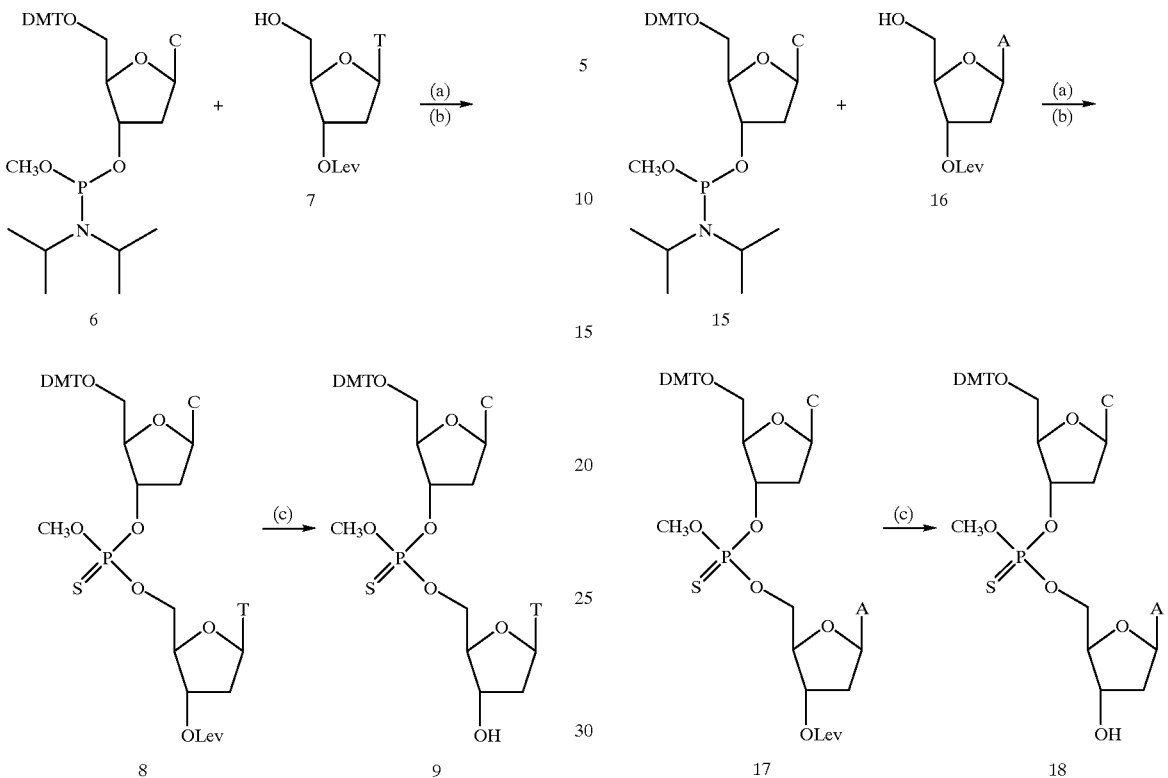

wherein (a) is acetonitrile and tetrazole, (b) is Beaucage reagent, and (c) is pyridine acetic acid and hydrazine hydrate. DMT is dimethoxytrityl and Lev is levulinyl.

A mixture of N4-benzoyl 5'-O-dimethoxytrityl-2'-deoxycytidine-3'-O-methyl N,N-diisopropyl phosphoramidite 6 (1.6 g, 2 mmol) and 3'-O-levulinyl-thymidine, 7, (0.68 g, 2 mmol) was dissolved in anhydrous acetonitrile (25 ml) and a solution of tetrazole (0.45 M, 10 ml) was added. The reaction mixture was stirred for 15 minutes at room temperature. Beaucage reagent (0.6 g in anhydrous acetonitrile 15 ml) was added and the reaction mixture was further stirred for 15 minutes. The reaction mixture was then evaporated to remove most of the solvent. The crude reaction product was extracted with dichloromethane and washed with brine to obtain 8. Dichloromethane was evaporated, the solid residue was re-dissolved in 20 ml pyridine and mixed with 20 ml of 1 M hydrazine hydrate solution in pyridine/acetic acid (3/2). The reaction mixture was stirred for 5 min. The reaction mixture was then cooled on an ice-bath and 4 ml acetyl acetone was added to quench the excess amount of hydrazine hydrate. The mixture was evaporated to a small volume and then directly applied to silica gel column chromatography (2.5×25 cm). The dimer block product, 9, was eluted by using 0–7% methanol in dichloromethane (0.5% pyridine) to obtain 1.25 g (67% yield). $^{31}$P NMR=69.86.

Example 3
Solution Phase Synthesis Of 5'-O-dimethoxytrityl-N$^4$-benzoyl-2'-deoxycytidine-3'-O-methylphosphorothioate 5'-O-N$^6$-benzoyl-2 ' deoxyadenosine The synthetic steps for this dimer block for synthesis of phosphorothioate-containing oligonucleotides are shown below:

wherein (a)–(c) are the same as in Example 2.

A mixture of N$^4$-benzoyl-5'-O-dimethoxytrityl-2'-deoxycytidine-3'-O-methyl N,N-diisopropyl phosphoramidite, 15, (4 g, 5 mmol) and 3'-O-levulinyl-N$^6$-benzoyl-2'-deoxyadenosine, 16, (2 g, 4.4 mmole) was dissolved in anhydrous acetonitrile (18 ml) and a solution of tetrazole (0.45 M, 22 ml) was added. The reaction mixture was stirred for 30 minutes at room temperature, then treated with Beaucage reagent (1.4 g in anhydrous acetonitrile 25 ml) for 15 minutes. The reaction mixture was then evaporated to remove most of the solvent. The crude reaction product was extracted with dichloromethane and washed with brine. Dichloromethane was evaporated to obtain a solid product, 17, which was then redissolved in 40 ml pyridine, and 40 ml of 1 M hydrazine hydrate solution in pyridine/acetic acid (3/2) was added. After 7 minutes, the reaction was quenched with ice and the product was extracted with dichloromethane, then washed with water. The organic layer was dried over sodium sulfate and then co-evaporated with toluene to dryness. The mixture was re-dissolved in a small volume of dichloromethane and applied to silica gel column chromatography (5×12 cm). The dimer block product, 18, was eluted by using 0–7% methanol in dichoromethane (0.5% pyridine) to obtain 3.8 g (79% yield). $^{31}$P NMR=69.84, 69.89.

Example 4
Synthesis of N-benzoyl-5'-O-dimethoxytrityl-P-cyanoethylthiophosphoryl-2'-deoxycytidylyl-3'-O-[(N,N-diisopropylamino)cyanoethoxyphosphino](3'→5') thymidine (24)

The title phosphoramidite dimer was synthesized as depicted below:

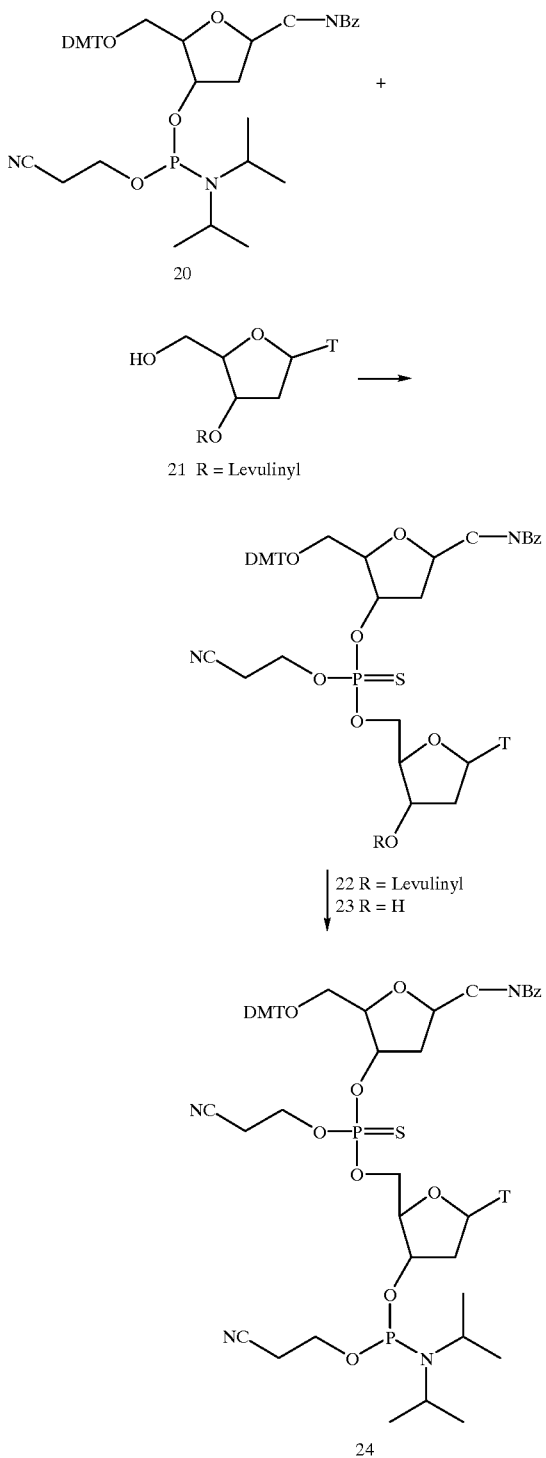

Synthesis of dimer 22

60 ml of 0.45 M solution of tetrazole in acetonitrile were added to a solution of phosphoramidite 20 (10.0 g, 12.0 mmol) and nucleoside 21 (4.0 g, 12.0 mmol) in 150 ml acetonitrile. The reaction was stirred for 30 min at room temp. TLC analysis indicated that complete conversion of the starting materials to the intermediate phosphite, which was further oxidized by adding 88 ml acetonitrile solution of Beaucage Reagent (3.52 g, 18.0 mmol). The reaction was stirred for 30 min and then was evaporated to dryness in vacuo to give dimer 22 as a yellow gum in quantitative yield (13.0 g, $^{31}$P NMR, δ 67.0).

Synthesis of dimer 23

Hydrazine monohydrate (2.1 g, 42.0 mmol) was added slowly to an ice-cold solution of crude dimer 22 (6.63 g, 6.0 mmol) in 65 ml pyridine/acetic acid mixture (3:2). After 20 min, excess hydrazine monohydrate was quenched with the slow addition of acetyl acetone (11 ml). The reaction was added to crushed ice and was extracted with methylene chloride (3×50 ml). Combined organic layer was dried and evaporated to give a yellow oil, which was chromatographed on flash silica gel. Elution with methylene chloride/methanol/pyridine (93:5:2) gave dimer 23 as a colorless foam (5.0 g, 82.7% $^{31}$P NMR, δ, 67.0).

Synthesis of dimer 24

A solution of dimer 23 (31.5 g, 31.3 mmol) and tetrazole (2.75 g, 39.3 mmol) in 150 ml acetonitrile was added to a solution of tetraisopropylphosphorodiamidite (13.0 g, 43.1 mmole) in 60 ml of acetonitrile. The reaction was stirred at room temperature for 45 minutes. It was then cooled in ice and the supernatant solution was decanted into another flask. The precipitate was washed with cold acetonitrile three times. The combined acetonitrile solution was evaporated to dryness. The residue was dissolved in dichloromethane and hexane was added. Supernatant solution was removed and the residual oil was washed with hexane. The dichloromethane/hexane treatment was repeated one more time. The resulting yellow foam was dissolved in ethyl acetate containing I% pyridine and was passed quickly through a short pad of silica gel. Evaporation of the pooled fractions afforded the dimer phosphoramidite 24 as colorless foam (31.7 g, 83.9%, $^{31}$P, δ, 67.0 (P-V), ~149.0 (P-III).

Example 5

Determining the purity of phosphorothioate dimers

Authentic samples of CpoT dimer phosphoramidites were made by employing the same chemistry as that used to synthesize CpsT dimer phosphoramidites, except that t-butyl hydroperoxide was used instead of Beaucage reagent to oxidize the phosphite intermediate to give the phosphotriester dimer.

Phosphotriester and phosphorothioate dimers can be distinguished by $^{31}$P NMR. The phosphoramidite phosphorous signal in both cases appears at ~δ 149. There is a significant difference in the chemical shifts of the phosphorothioate and phosphotriester functions, however. Phosphorothioate triester signal is observed at ~δ 67.0, whereas the phosphotriester peak appears at ~δ −2.0. A trace amount of H-phosphonate byproduct is detected in the phosphorothioate dimer as a doublet centered at δ 14.5. Thus, $^{31}$P NMR can serve as an effective tool in determining the impurity of phosphotriester in a phosphorothioate triester compound.

Two samples of phosphorothioate dimer phosphoramidite were spiked with a known amount of phosphotriester dimer phosphoramidite. A sample containing 10% phosphotriester dimer and 90% of phosphorothioate dimer and a second sample constituting 5% phosphotriester dimer and 95% phosphorothioate dimer were prepared and the $^{31}$P NMR of the samples recorded. $^{31}$P NMR spectra of both samples exhibited distinct, well-separated signals at ~δ 67.0 and ~δ

−2.0, as expected. A 750 times enlargement of pure phosphorothioate dimer spectrum manifested no detectable peak at ~δ 2.0.

Example 6

0.2 µmol scale synthesis of oligonucleotide phosphorothioates

A fluidized bed technique was used for the synthesis of $(CT)_{10}T$ oligomer on a Perseptive Biosystem Expedite Synthesizer. The design of the synthesizer is such that the reagents like activator, amidite, and Cap A, Cap B are mixed before entering the column containing resin. There were two capping steps in this method, one before oxidation and another after oxidation. 37.6 equivalents of dimer were used in each coupling step.

In this and all subsequent oligonucleotide syntheses described herein, the dimer phosphoramidite was made as described in Example 4. All other reagents were purchased from commercial sources and used as received. Fresh solutions of the reagents were made prior to the start of the oligonucleotide synthesis. At the end of the synthesis, resin was dried under vacuum. The oligonucleotide was cleaved from the support and deprotected by treating it with ammonium hydroxide at 55° C. overnight. Crude product was analyzed by reverse phase chromatography, ion exchange chromatography and capillary gel electrophoresis.

Detritylation

3% trichloroacetic acid in dichloromethane were used for detritylation in three steps:

a) 0.3 ml was delivered for 8 sec.;

b) 0.3 ml was delivered for 8 sec.; and c) 0.45 ml was delivered for 30 sec.

Wash

Washing was conducted with acetonitrile. 0.9 ml was delivered for 30 sec.

Coupling

The activator used for coupling was 0.45 M 1-H tetrazole in acetonitrile; the amidite was 0.1 M solution of dimer phosphoramidite in acetonitrile. Coupling was conducted as follows:

a) pre-couple wash with acetonitrile—0.075 ml for 1 see;

b) 0.075 ml activator was introduced for 1 sec;

c) 0.075 ml activator was delivered for 1 sec;

d) 0.075 ml amidite was delivered for 1 sec;

e) 0.075 ml activator was introduced for 1 sec;

f) 0.090 ml acetonitrile wash for 2.4 sec;

g) coupling was allowed to continue for 900 sec.

Wash

The resin was washed with 0.27 ml for 900 sec.

Capping

Cap A consisted of 10% acetic anhydride in tetrahydrofuran. Cap B was 10% N-methylimidazole, 20% pyridine, and 70% tetrahydrofuran. 0.12 ml of Cap A was delivered for 3 sec followed by delivery of 0.12 ml of Cap B for 3 sec.

Wash

The reaction mixture was then washed with 0.375 ml of acetonitrile for 17 sec.

Sulfurization 0.45 ml of 2% Beaucage reagent in acetonitrile was delivered for 7 sec.

Wash

The reaction mixture was then washed with 0.3 ml of acetonitrile delivered for 120 sec.

Capping 0.105 ml of each of Cap A and Cap B was delivered for 2 sec.

Wash

The reaction mixture was then washed with 0.9 ml of acetonitrile delivered for 15 sec.

Example 7

15 µmole scale synthesis of oligonucleotide phosphorothioates

The same solutions were used as described previously in this Example to synthesize the $(CT)_{10}T$ oligomer on a 15 µmol scale. 5.02 equivalents of dimer were used in each coupling step.

Detritylation 7.5 ml detritylation solution was delivered for 200 sec.

Wash

Washing was conducted in two steps:

a) 0.75 ml of acetonitrile was delivered for 12.5 sec; and b) 6.0 ml of acetonitrile was delivered for 100 sec.

Coupling a) 0.6ml acetonitrile as a pre-couple was added for 16 sec;

b) 0.525 ml activator was delivered for 14 sec;

c) 0.375 ml amidite was delivered for 10 sec;

d) 0.375 activator was delivered for 10 sec;

e) pause for 60 sec;

f) 0.3 ml activator was delivered for 30 sec;

g) 0.6 ml acetonitrile wash for 10 sec;

h) 0.375 ml amidite was delivered for 10 sec;

i) 0.375 ml activator was delivered for 10 sec;

j) pause for 60 sec;

k) 0.3 ml activator was delivered for 30 sec;

l) coupling was allowed to continue for an additional 900 sec.

Wash

Washing was conducted in two steps:

a) 1.5 ml of acetonitrile was delivered for 40 sec; and b) 1.5 ml of acetonitrile was delivered for 25 sec.

Capping a) 1.125 ml Cap A was delivered for 30 sec;

b) 1.125 ml Cap B was delivered for 30 sec.

Wash a) 0.225 ml acetonitrile wash for 40 sec, followed by b) 1.5 ml acetonitrile wash for 25 sec.

Sulfurization a) 1.875 ml of Beaucage solution was added over 50 sec and allowed to react for 60 sec.

Wash a) 1.5 ml of acetonitrile wash was added for 25 sec.

Capping a) 0.750 ml Cap A was delivered for 20 sec.

b) 0.750 ml Cap B was delivered for 20 sec.

Wash a) 5.1 ml acetonitrile was added for 85 sec.

Example 8

300 µmole scale synthesis of oligonucleotide phosphorothioates

Syntheses of $(CT)_{10}T$ oligomer was conducted on a 300 µmol scale on a Pharmacia OligoPilot II Synthesizer. CPG-T was purchased from Glen Research (Sterling, Va.).

Flow-through type column reactor was used for the synthesizer. CPG-T support was packed in the column. The amount and the rate at which the reagent was delivered to the reactor column depended on the scale of the synthesis and the size of the column.

In one synthesis, 10.5 g CPG-T (29.0 μmol/g) was used in a 46 ml size column. Two equivalents of dimer phosphoramidate were used in each coupling step for all 300 μmol scale syntheses. The synthesis cycle consisted of the following steps:

Detritylation

3% dichloroacetic acid in dichloroethane was passed through the solid support for 3 minutes at a rate of 75 ml/min.

Wash

Washing was conducted in two steps:
  a) Acetonitrile was passed through the column for 6 min at a rate of 75 ml/min.
  b) Acetonitrile was passed through the column for 1.92 min at a rate of 75 ml/min.

Coupling

The activator solution and the amidite solution were injected in alternate fashion. The activator solution was introduced to the reactor for 1 min at a rate of 36 ml/min. This process was repeated eight times. The amidite solution was introduced for 0.2 min at a rate of 3.8 ml/min. This process was also repeated eight times. Again the activator solution was pumped for 0.1 min at a rate of 36 ml/min. The line to the reactor was washed with acetonitrile for 0.1 min at a rate of 4 ml/min. This activity was repeated 8 times. Combined solution of the activator and the amidite was then circulated in the reactor loop for 6 min at a rate of 25 ml/min.

Wash

The column was washed with acetonitrile for 2 min at a rate of 25 ml/min.

Sulfurization

5% Beaucage reagent in acetonitrile was introduced to the column for 0.6 min at a rate of 48 ml/min. The line was washed with acetonitrile for 0.1 min at a rate of 15 ml/min. The Beaucage solution was circulated in the loop for 5 min at a rate of 50 ml/min.

Wash

The column was washed with acetonitrile for 1 min at a rate of 50 ml/min.

Capping

The two capping solutions used comprised:
  Cap A: 20% N-methylimidazole in acetonitrile; and
  Cap B: 20% acetic anhydride, 30% sym-collidine, 50% acetonitrile.

Cap A and Cap B solutions were pumped into the reactor alternatively. Cap A solution was introduced for 0.1 min at a rate of 18 ml/min. This action was repeated eight times. Cap B solution was also injected for 0.1 min at a rate of 18 ml/min. This process was repeated eight times.

Wash a) The first wash step was done for 4.17 min at a rate of 14.4 ml/min.
  b) This next wash step was performed for 1.28 min at a rate of 75 ml/min.

Example 9

300 μmole scale synthesis of oligonucleotide phosphorothioates without capping This synthesis of the $(CT)_{10}T$ oligomer was conducted using 8.0 g of CPG-T (38.0 μmol/g) in a 24 ml size reactor. The reagents used for this synthesis were the same as those described in Example 8, but, as seen in the protocol below, a capping step was not employed. Two equivalents of dimer were used for each coupling step. The synthesis cycle is described below.

Detritylation

The detritylation solution was passed through the solid support for 3 min a rate of 50 ml/min.

Wash a) The column was washed with acetonitrile. Acetonitrile was passed through the column for 6 min at a rate of 50 ml/min.
  b) This wash utilized acetonitrile for 1.44 min at a rate of 50 ml/min.

Coupling

The activator solution and the amidite solution were injected in alternate fashion. The activator solution was introduced to the reactor for 0.1 min at a rate of 24 ml/min. This process was repeated six times. The amidite solution was introduced for 0.2 min at a rate of 4.8 ml/min. This process was also repeated six times. Again the activator solution was pumped for 0.1 min at a rate of 24 ml/min. The line to the reactor was washed with acetonitrile for 0.1 min at a rate of 4 ml/min. This activity was repeated eight times. Combined solution of the activator and the amidite was then circulated in the reactor loop for 6 min at a rate of 20 ml/min.

Wash

The column was washed with acetonitrile for 1 min at a rate of 20 ml/min.

Sulfurization

Beaucage solution was introduced to the column for 0.6 min at a rate of 24 ml/min. The line was washed with acetonitrile for 0.2 min at a rate of 15 ml/min. The Beaucage solution was circulated in the loop for 4.6 min at a rate of 28.8 ml/min.

Wash

The column was washed with acetonitrile for 1 min at a rate of 24 ml/min.

Capping

The program for capping was not changed. The Cap A and Cap B bottles were filled with acetonitrile instead of the respective reagents. Thus, the capping step for this protocol becomes the wash step.

Wash a) This wash step was done for 1.25 min at a rate of 24 ml/min.
  b) This step was performed for 0.95 min at a rate of 50 ml/min.

The results of three different syntheses conducted without capping and before chromatographic purification are presented as experiment numbers 5–7 in Table 5, infra.

Example 10

Purification of $(CT)_{10}T$ prepared by dimer block synthesis

Oligonucleotides prepared according to the foregoing examples were subjected to chromatography to purify them further. Products taken for purification are described in Table 5, lines 3, 4, and 6. These products correspond to the three entries for Crude Product in Table 4. As shown, products corresponding to the first two entries in Table 4 were purified by RPC followed by IEX. Product corresponding to the third entry in Table 4 was purified using IEX as the sole chromatographic step. Following chromatography, desalted product was prepared by ultrafiltration/diafiltration and lyophilization, as required. Product of >98% purity was obtained, as determined by both analytical IEX-HPLC and capillary electrophoresis (CE). $^{31}$P NMR was employed to determine PO content.

The purification procedures described below were conducted using crude product prepared at the 15 µmol and 300 µmol scales. Experience obtained during work with the 15 µmol scale was applied to the subsequent purification at the 300 µmol scale resulting in enhanced purity.

Reversed Phase Chromatography

As noted, RPC was used for preliminary purification of crude oligonucleotide having lower purity, as synthesized. RPC was employed in purification of crude products described in the first two entries of Table 4, but was omitted in purifying crude product described in the third entry of this table. Crude product produced at 15µmole scale (with capping) is of higher purity than that produced at 300 µmol scale (with capping). The higher purity of the product obtained at 15 µmol scale probably arises from the greater excess of amidite (7–8 fold) employed during synthesis compared with that employed at 300 µmol scale (2-fold excess).

RPC was performed using Amberchrom CG-300sd (TosoHaas), a porous styrenic resin. A combination of gradient and isocratic elution was employed. Buffer A was 0.10 M aqueous ammonium acetate. Buffer B was 80/20 v/v/acetonitrile/Buffer A.

Chromatography at the 15 µmol scale was performed using a 1.0 cm ID×14.1 cm column. Load and wash steps were conducted at 4.0 ml/min; isocratic and gradient elution were conducted at 2.0 ml/min. At the 300 µmol scale, a 2.5 cm ID×20.3 cm column was employed. Two runs were made. During the first run, load and wash steps were performed at 24.5 ml/min; isocratic and gradient elution were conducted at 12.3 ml/min. During the second run, the flow rate was 12.3 ml/min throughout.

Feedstock was prepared by addition of Picopure water to the crude product in ammonium hydroxide solution; ammonium acetate was added to provide a concentration of 0.2 M. At the 15 µmol scale, feedstock had a concentration of approximately 20 $A_{260}$ units/ml solution. The loading factor was approximately 175 $A_{260}$ units/ml bed. At the 300 µmol scale, corresponding values were 53 $A_{260}$ unit/ml solution and 147 $A_{260}$ units/ml bed.

Purification was accomplished using the non-optimized sequence of steps displayed in Table 2. Capping was employed the synthesis of each of the samples shown.

TABLE 2

| # | 15 µmol scale | 300 µmol scale (run 1) | 300 µmol scale (run 2) |
|---|---|---|---|
| 1 | Load | Load | Load |
| 2 | Wash, 100% (A)[1], 5.4 CV[3] | Wash, 100% (A), 1.1 CV | Wash, 100% (A), 1.2 CV |
| 3 | Grad:[3] 0–21% (B)[2] @ 1%/min, 1.1 CV | Grad: 0–19% (B) @ 1%/min, 1.1 CV | Grad: 0–19% (B) @ 1%/min, 1.1 CV |
| 4 | Isocrat[3] 21% (B), 3.4 CV | Isocrat 19% (B), 1.8 CV | Isocrat 19% (B), 1.8 CV |
| 5 | Grad: 21–72% (B) @ 1%/min, 9.2 CV | Grad: 19–32% (B) @ 1%/min, 1.5 CV | Grad: 19–31% (B) @ 1%/min, 1.5 CV |
| 6 | Wash, 100% (B), 7.9 CV | Isocrat 32% (B) 1.1 CV | Isocrat 31% (B) @ 1%/min, 1.2 CV |
| 7 | — | Grad: 32–55% (B) @ 1%/min, 2.5 CV | Grad: 31–55% (B) @ 1%/min, 2.5 CV |
| 8 | — | Wash, 100% (B), Approx. 4 CV[4] | Wash, 100% (B), Approx. 4 CV[4] |

[1]"A" refers to Buffer A (0.1 M ammonium acetate)
[2]"B" refers to Buffer B (80/20 v/v acetonitrile/Buffer A)
[3]"CV" is column volume, "Grad" is gradient elution, and "isocrat" is isocratic elution.
[4]The initial 1.5 CV was collected as a chromatographic fraction, the remainder was diverted to waste.

Pooled chromatographic fractions were drawn from the fourth and fifth steps in the 15 µmol scale purification and from the sixth step in the 300 µmol scale purifications.

Detritylation

Crude product corresponding to the third entry in Table 4 was subjected to IEX purification without preliminary RPC purification. First, however, crude product in ammonium hydroxide solution was processed on a rotary evaporator to remove ammonia prior to detritylation. To the remaining solution, a quantity of pure water was added, as required, to yield a solution having $A_{260} \leq 50$ OD/ml. Finally, a quantity of glacial acetic acid was added to provide a final concentration of 20% V/V glacial acetic acid. The resulting solution was stirred at room temperature for 2.5 hr.

Post-RPC pools were detritylated in a corresponding procedure, but excluding processing on a rotary evaporator. After addition of glacial acetic acid, the reaction period was 2.25 hr at the 15 µmol scale and 2.75 hr at the 300 µmol scale.

After these procedures, the oligonucleotide products were subject to IEX.

Ion Exchange chromatography

IEX was performed using TSK-GEL DEAE-5PW (TosoHaas), a DEAE-substituted methacrylic polymer. A combination of gradient and isocratic elution was employed. Buffer A was 25 mM TrisCl, pH 7.2. Buffer B was 25 mM TrisCl containing 2.0 M sodium chloride, pH 7.2.

The detritylated oligonucleotides previously subjected to RPC were purified as follows:

At the 15 µmol scale, a column 0.66 cm ID×13. 3 cm was employed. Steps 1, 2, and 7 (Table 3), were conducted at 1.29 ml/min, while steps 3–6 were conducted at 0.86 ml/min. The loading factor was 212 $A_{260}$ units/mi bed.

At the 300 µmol scale, a column 2.2 cm ID×19.0 cm was employed. Steps 1, 2, and 7 (Table 3) were conducted at 14.3 ml/min, while steps 3–6 were conducted at 9.5 ml/min. The loading factor was 217 $A_{260}$ units/ml bed.

Crude detritylated oligonucleotide that had not been subjected to RPC was purified using a column 1.1 cm ID×8.3 cm. Steps 1 and 2 were conducted at 3.6 ml/min., while steps 3–10 were conducted at 2.4 ml/min (Table 3). The loading factor was 249 $A_{260}$ units/ml bed.

The non-optimized elution steps listed in Table 3 were employed:

TABLE 3

| 15 μmol scale[3] (capping) | 300 μmol scale[3] (capping) | 300 μmol scale[4] (no capping) |
|---|---|---|
| 1 LOAD | LOAD | LOAD |
| 2 Wash, 100% (A)[1], 7.7 CV[5] | Wash, 100% (A), 6.6 CV | Wash, 100% (A), 8.5 CV |
| 3 Grad.[5], 10–40% (B)[2] @ 0.5%/min., 11.2 CV | Grad., 20–30% (B) @ 0.5%/min., 4.0 CV | Isocrat.[5], 22% (B), 3.2 CV |
| 4 Isocrat. 40% (B), 3.7 CV | Isocrat. 35% (B), 3.6 CV | Isocrat. 30% (B), 10.5 CV |
| 5 Grad., 40–60% (B) @ 0.5%/min., 7.4 CV | Grad., 35–52% (B) @ 0.5%/min., 4.5 CV | Isocrat., 36% (B), 5.1 CV |
| 6 Isocrat., 75% (B), 2.2 CV | Grad., 52–75% (B) @ 1%/min., 3.0 CV | Isocrat. 46% (B), 5.9 CV |
| 7 Isocrat., 100% (B), 5.0 CV | Isocrat., 75% (B), 6.1 CV | Isocrat., 52% (B), 7.5 CV |
| 8 — | Isocrat., 100% (B), 4.0 CV | Isocrat., 58% (B), 6.6 CV |
| 9 — | — | Isocrat., 75% (B), 3.2 CV |
| 10 — | — | Isocrat., 100% (B), 5.1 CV |

[1]"A" refers to Buffer A (0.3 NaOH)
[2]"B" refers to Buffer B (0.3 NaOH + 2.0 NaCl)
[3]detritylated, post-RPC pool
[4]detritylated crude product
[5]CV = column volume, "Grad" is gradient elution, and "Isocrat" is isocratic elution Pooled fractions were drawn from steps 4–7 in the 15 μmol scale synthesis, steps 6–7 (pool 1) and 5–7 (pool 2) in the 300 μmol scale synthesis with capping, and steps 5–8 (pool 1) and 6–9 (pool 2) in the 300 μmol scale synthesis without capping.

In order to achieve purities ≧98% as measured by both IEX-HPLC and CE, it was necessary to make rigorous use of CE analysis during pooling decisions. Trial pools were prepared from chromatographic fractions so as to provide 99% and/or 98% purity as determined by IEX-HPLC. Various subsets of these trial pools were then prepared using a more restricted range of chromatographic fractions. These subsets were then analyzed by CE to assure that they met 98% or 99% purity goals, as required. This approach was successfully employed during purification of crude products prepared at 300 μmole scale. Pools of 98% and 99% purity were isolated, as determined by both IEX-HPLC and CE, and (n+x) values were reduced to 0.3% or less. This rigorous use of CE analysis was not employed during purification of product prepared at 15 μmole scale. Here, CE purity of the product was 97%, and (n+x) content was 2.4%.

Desalting and Lyophilization

As required, desalting was performed by diafiltration using an Amicon stirred cell fitted with a 1000 MWCO membrane. Conductivity of the final diafiltrate was reduced to <60 μmho. Lyophilization of the desalted solution followed.

The results presented in Table 4 and 5 below are based, in part, on definitions and formulae set forth in the "Detailed Description of the Invention" section, particularly the section "Ultrapure Oligonucleotides." Selected definitions and formulae are presented or restated in footnotes to these tables for clarity. Additional definitions, formulae, and calculation procedures are presented in the text immediately following Table 4.

TABLE 4

| | | | Purity | | | | | | | % Recovery After Chromatog. |
|---|---|---|---|---|---|---|---|---|---|---|
| | | | | | % Purity by CE | | | | | |
| Scale (μmol) | % DMT-on RP[11] | % DMT-on IEX[3] | % Purity IEX[4] | N | N − 1 | N − 2 | Σ N − x (X > 2) | Σ N + x | % PO[12] | Step (by IEX) |
| Crude Product | | | | | | | | | | |
| 15[1] | 82 | 80 | 65[9] | 74 | ND | 4.6 | 18.8 | 3.0 | — | |
| 300[1] | 83 | 75 | 65[9] | 65 | 0.8 | 2.4 | 25.3 | 7.0 | — | |
| 300[2] | 83 | 88 | 81[9] | 80 | 0.7 | 3.9 | 12.0 | 3.4 | — | |
| Purification by RPC (on Amberchrom CG-300sd) | | | | | | | | | | |
| 15[1] | — | 93 | 73[9] | — | — | — | — | — | — | 70[7] |
| 300[1]: | | | | | | | | | | |
| Run 1 | — | see pool | see pool | — | — | — | — | — | — | 59[7] |
| Run 2 | — | see pool | see pool | — | — | — | — | — | — | 63[7] |
| Pool Runs 1 + 2 | — | 86 | 76[9] | — | — | — | — | — | — | 61[7] |
| 300[2] | N/A[5] | N/A | N/A | N/A | N/A | N/A | N/A | N/A | N/A | N/A |
| Detritylation (Analysis of reaction mixture) | | | | | | | | | | |
| 15[1] | — | — | 71[10] | — | — | — | — | — | — | |
| 300[1] | — | — | 77[10] | 87 | — | — | — | — | — | |
| 300[2] | — | — | 73[10] | — | — | — | — | — | — | |
| Purification by IEX (on DEAE-5PW) | | | | | | | | | | |
| 15[1] | — | — | 98[10] | 97 | ND[6] | 0.8 | ND | 2.4 | 1.0 | 88[8] |
| 300[1]: | | | | | | | | | | |
| Pool 1 | — | — | 98[10] | 98 | ND | 0.5 | 1.5 | 0.1 | 0.2 | 76[8] |

TABLE 4-continued

| | | | | Purity | | | | | | | % Recovery After Chromatog. |
|---|---|---|---|---|---|---|---|---|---|---|---|
| | | | | | | % Purity by CE | | | | | |
| Scale (µmol) | % DMT-on RP[11] | % DMT-on IEX[3] | % Purity IEX[4] | N | N − 1 | N − 2 | ΣN − x (X > 2) | ΣN + x | % PO[12] | Step (by IEX) |
| Pool 2 300[2]: | — | — | 99[10] | 99 | ND | 0.4 | 0.5 | 0.2 | 0.4 | 54[8] |
| Pool 1 | — | — | 98[10] | 99 | ND | 1.2 | 0.2 | ND | 0.6 | 69[8] |
| Pool 2 | — | — | 99[10] | 99 | ND | 0.7 | 0.2 | 0.3 | 0.0 | 47[8] |

[1] with capping
[2] without capping
[3] $[\alpha_N + \alpha_{PO/N-x}]_{IEX,DMT\text{-}on}$
[4] $[\alpha_N]_{IEX}$
[5] N/A = not applicable
[6] ND = not detected
[7] % recovery of DMT-on form. Calculated as described in text below.
[8] % recovery of product expressed as IEX units. Calculated as described in text below.
[9] Analysis of DMT-on form
[10] Analysis of DMT-off form
[11] $[\alpha_N]_{RP}$
[12] Estimated % PO Chromatographic recoveries presented in Table 5 are expressed in two forms. Recovery after RPC purification is expressed with respect to the DMT-on form as percent RPC units recovered. Recovery after IEX purification is expressed as percent IEX units of product (DMT-off) recovered. RPC units and IEX units present in a quantity of the stock (i.e., load) or in individual or pooled fractions may be calculated as follows:

(1) calculate the number of $A_{260}$ units in a given volume of solution:

($A_{260}$ units)=(ml of solution) ($A_{260}$ determined using 1 cm path cuvette)

(2) determine the percent purity by analytical IEX or analytical RPC:

(3) calculate RPC units in a given volume of solution:

(RPC units)=[(A 260 units) (% DMT-on purities by RPC)]/100

(4) calculate IEX units in a given volume of solution:

(IEX units)=[($A_{260}$ units)(% purity by IEX)]/100

Using the above values, chromatographic recoveries are calculated:

(1) calculate percent recovery of DMT-on form:

$$[\% \text{ Recovery}]_{DM-on} = \frac{(RPC \text{ units in pool})}{(RPC \text{ units in load})} \times 100$$

(2) calculate percent recovery of product as IEX units:

$$[\% \text{ Recovery}]_{IEX} = \frac{(IEX \text{ units in pool})}{(IEX \text{ units in load})} \times 100$$

The overall chromatographic yield for the two step purification (defined as "(% recovery DMT-on by RPC)×(% recovery by IEX)) was 62% at the 15 µmol scale and 46% and 29% for pools 1 and 2, respectively, at the 300 µmol scale (with capping). The overall chromatographic yield for the single-step purification is identical to % recovery by IEX and was thus 69% and 47% for pools 1 and 2, respectively, obtained after purification at the 300 µmol scale (no capping).

Values for estimated %PO in Table 4 were calculated as set forth in the "Detailed Description of the Invention" section, under the heading "Ultrapure Oligonucleotides." Purified product described in the final entry of Table 4 (Pool2, 300 µmol scale, without capping) was also analyzed by $^{31}$P NMR to determine PO content. In this analysis no PO was detected.

Additional 21-mer oligonucleotides were synthesized according to the foregoing protocols. The results are presented in Table 5. The oligonucleotide was obtained in the range of 65–81% as detected by capillary electrophoresis (see Table 5). Interestingly, in experiment 2, when 75% of the 21-mer was observed, the N−1 content was undetectably small. The average stepwise coupling yield in experiment 2 was 97.2%. Ion-exchange chromatography estimates of the phosphodiester content per linkage in the phosphorothioate 21-mer was generally below 1.0%.

The average stepwise coupling yield for the 15.0 µmol scale synthesis was 97.0%, whereas for the 300 µmol scale synthesis it was 97.2%.

TABLE 5

| # | Scale (µmol) | ODs | % RP | % IEX DMT-on | % CE N | N − 1 | N − 2 | N + x | % PO (IEX) |
|---|---|---|---|---|---|---|---|---|---|
| 1* | 0.2 | 24 | 84 | 86 | 65 | 10.6 | 3.11 | 5.7 | 0.7 |
| 2 | 0.2 | 23 | 87 | 81 | 75 | ND | 5.4 | 4.9 | 1.2 |
| 3 | 15.0 | 1700 | 82 | 80 | 74 | ND | 4.6 | 3.0 | 0.9 |
| 4 | 300 | 30000 | 83 | 75 | 65 | 0.8 | 2.4 | 7.0 | 0.7 |
| 5 | 289 | 30894 | 79 | 72 | 75 | 1.1 | 2.3 | 7.4 | 0.4 |
| 6 | 304 | 33360 | 83 | 87 | 80 | 0.7 | 3.9 | 3.4 | 0.4 |
| 7 | 304 | 33583 | 87 | 87 | 81 | 0.6 | 3.1 | 3.9 | 0.4 |

*monomer synthesis
ND = not detectable

We claim:

1. A method of manufacturing a N-mer oligonucleotide composition of ultrahigh purity, the method comprising a) synthesizing the oligonucleotide with dimer blocks using phosphoramidite chemistry, said synthesis comprising contacting a nascent oligonucleotide with 6 or fewer equivalents of a phosphoramidite dimer block, oxidation, detritylation, and repeating each the foregoing steps in this part (a) until the N-mer oligonucleotide is obtained;

b) subjecting the full-length, N-mer oligonucleotide synthesized in part (a) to (i) ion-exchange chromatography or to (ii) either reversed phase or hydrophobic interaction chromatography followed by ion-exchange chromatography;

c) pooling chromatographic fractions from part (b) having equal to or greater than 99% total purity of N-mer oligonucleotide.

* * * * *